United States Patent [19]

Ayer et al.

[11] 4,018,918

[45] Apr. 19, 1977

[54] TOPICAL CLINDAMYCIN PREPARATIONS

[75] Inventors: Donald E. Ayer; Carl A. Schlagel, both of Kalamazoo; Gordon L. Flynn, Ann Arbor, all of Mich.

[73] Assignee: The Upjohn Company, Kalamazoo, Mich.

[22] Filed: Mar. 19, 1976

[21] Appl. No.: 668,389

Related U.S. Application Data

[63] Continuation-in-part of Ser. No. 579,177, May 20, 1975, Pat. No. 3,980,778, which is a continuation of Ser. No. 409,427, Oct. 25, 1973, abandoned, which is a continuation-in-part of Ser. No. 316,973, Dec. 20, 1972, abandoned, which is a continuation-in-part of Ser. No. 233,337, March 9, 1972, abandoned.

[52] U.S. Cl. .................. 424/240; 260/239.55 R; 260/397.45; 260/239.55 D
[51] Int. Cl.² ................................ A61K 31/56
[58] Field of Search .................. 424/243, 240; 260/397.45

[56] References Cited

UNITED STATES PATENTS

| | | | |
|---|---|---|---|
| 3,312,590 | 4/1967 | Elks et al. | 167/58 |
| 3,312,591 | 4/1967 | Elks et al. | 167/58 |
| 3,557,158 | 1/1971 | Lincoln et al. | 260/397.45 |

*Primary Examiner*—Elbert L. Roberts
*Attorney, Agent, or Firm*—Bruce Stein; Roman Saliwanchik

[57] ABSTRACT

Disclosed is an anti-inflammatory compound, $6\alpha,9\alpha$-difluoro-$11\beta,17\alpha,21$-trihydroxy-$16\beta$-methylpregna-1,4-diene-3,20-dione 17,21-diacetate, and topical pharmaceutical formulations which include antimicrobial agents.

10 Claims, No Drawings

TOPICAL CLINDAMYCIN PREPARATIONS

CROSS REFERENCE TO RELATED APPLICATIONS

This application is a continuation-in-part of application Ser. No. 579,177, filed May 20, 1975, now U.S. Pat. No. 3,980,778; which is a continuation of application Ser. No. 409,427, filed Oct. 25, 1973, and now abandoned which is a continuation-in-part of application Ser. No. 316,973, filed Dec. 20, 1972, and now abandoned; which is a continuation-in-part of application Ser. No. 233,337, filed Mar. 9, 1972, and now abandoned.

BACKGROUND OF THE INVENTION

The compound, $6\alpha, 9\alpha$-difluoro-$11\beta, 17\alpha, 21$-trihydroxy-$16\beta$-methylpregna-1,4-diene-3,20-dione (10) and the 21-acetate are disclosed in U.S. Pat. No. 3,557,158 and are described as possessing anti-inflammatory properties.

A variety of steroid compounds have found use as local or topical anti-inflammatory agents. These are usefully administered to man and animals in convenient pharmaceutical forms such as creams, lotions, ointments, solutions, suspensions, drops, aerosols, dusting powders, suppositories and the like and cause reduction of the inflammatory process in situ for example in skin disorders, being used to control corticosteroid-responsive dermatoses such as psoriasis, eczema, seborrheic dermatitis, allergic contact dermatitis, providing symptomatic relief.

Clindamycin is known, and has been disclosed for topical use with anti-inflammatory steroids, but not with the anti-inflammatory steroid of the present disclosure. See U.S. Pat. Nos. 3,509,257; 3,155,580; and 3,539,689.

A somewhat anomalous reduction in effectiveness in open or non-occluded applications as compared with occluded applications is characteristic of most of the prior corticosteroids used as above as topical anti-inflammatory agents. Hence, to realize the full potential of most prior anti-inflammatory corticosteroids on the skin, the inconvenience of occluded application is commonly used despite the increased effort, the difficulty of wrapping the affected area and restrictive effect of the occluded application upon the patient.

SUMMARY OF THE INVENTION

The compound of this invention (1) can be prepared for administration as a local or topical anti-inflammatory in any of the conventional pharmaceutical forms noted above. It displays a high level of potency, permitting comparatively reduced concentration when applied being highly effective over the entire spectrum of diseases for which local or topical corticosteroids have heretofore been used. In addition, and of great medical and practical significance, its effectiveness is higher in non-occluded form on the skin than that of closely related corticosteroids tested, such as fluocinolone acetonide, and betamethasone valerate.

The compound of this invention, and appropriate pharmaceutical preparations containing effective levels of it can be used to control and reduce the inflammatory process in man and in other warm-blooded animals, and hence can be used in human and veterinary therapy particularly where local or topical anti-inflammatory effect is indicated, but also orally or parenterally for systemic effect for the relief of rheumatic, allergic, dermatological and ocular conditions generally responsive to anti-inflammatory agents. More specifically, the compositions of the present invention are useful for the reduction of symptoms in gout arthritis, rheumatoid arthritis, rheumatoid spondylitis, steoarthritis, psoriatic arthritis, acute superficial thrombophlebitis and painful shoulder syndromes such as peritendinitis, capsulitis, bursitis, and acute shoulder dermatitis, neurodermatitis, anogential pruritus, seborrheic dermatitis, and the like.

The antimicrobial compositions of this invention in appropriate pharmaceutical dosage forms are useful in treating various types of infected dermatoses. They are useful in treating bacterial or fungal infections and in treating mixed infections caused by both bacteria and fungi when accompanied by inflammation. Clinically, it is often impractical or impossible to determine whether a topical lesson is infected by either bacterial or fungal microorganisms. It is also possible that a primary bacterial infection may subsequently become secondary fungal infection and vice versa. Therefore, the combination of an antibacterial and an antifungal agent with the anti-inflammatory steroid is very useful to those treating such infections.

The compound of this invention can be prepared according to the following series of chemical steps.

ROUTE A

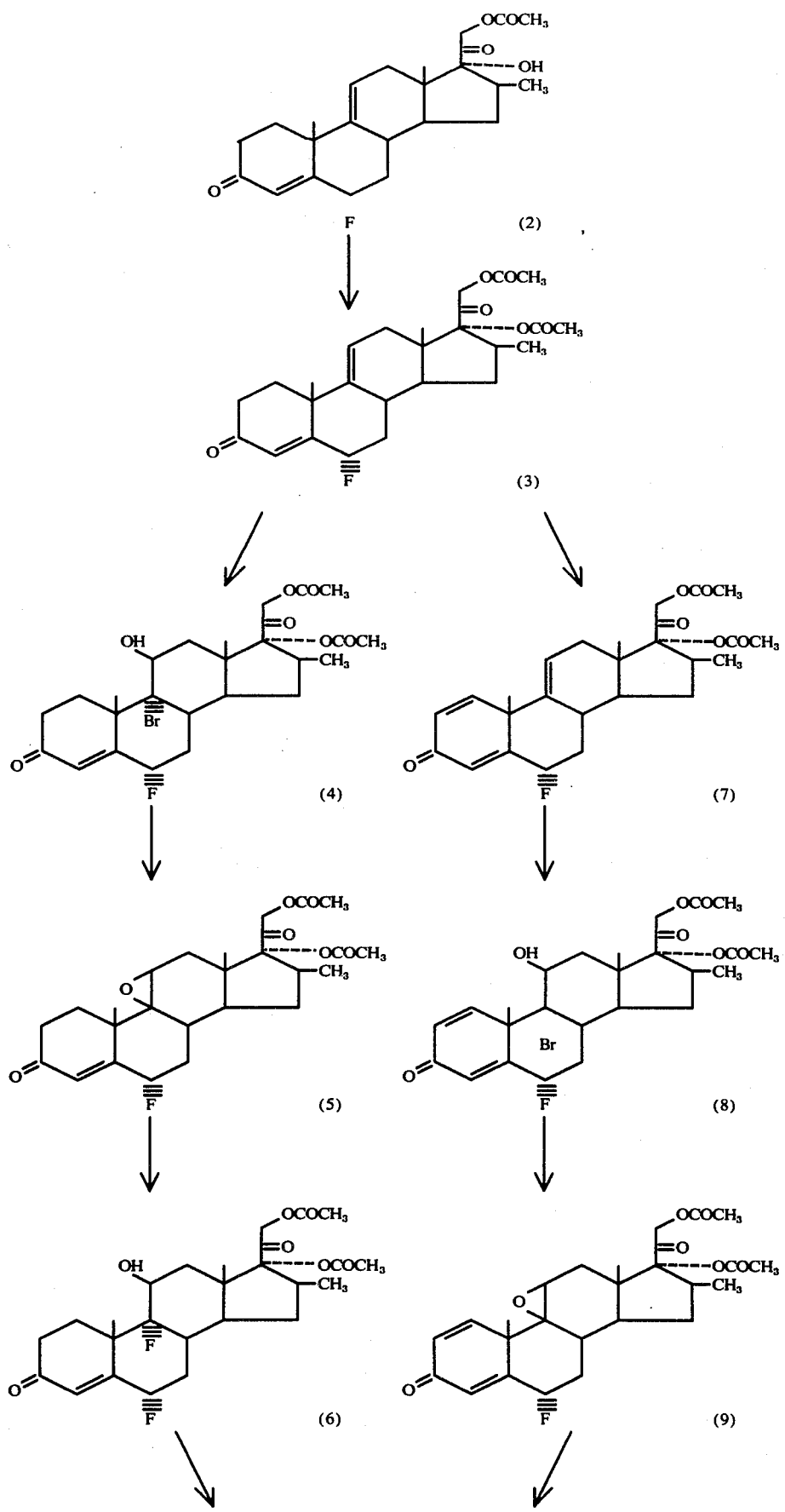

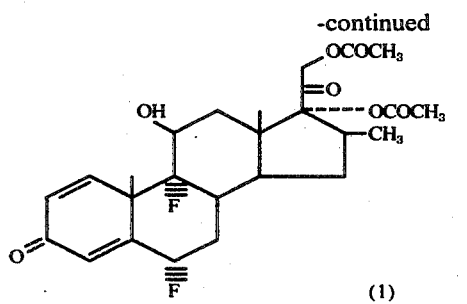
(1)
ROUTE B
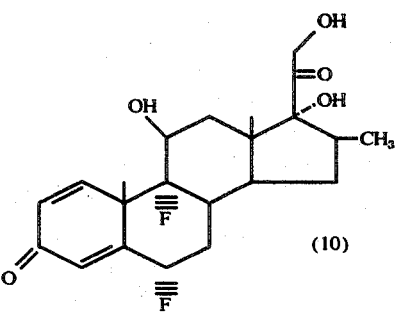
(10)
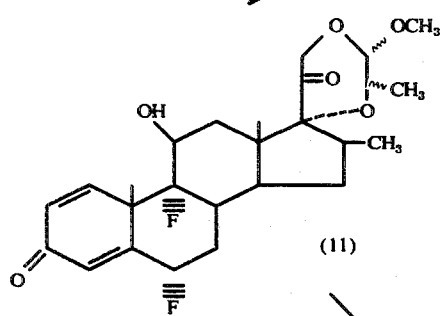
(11)
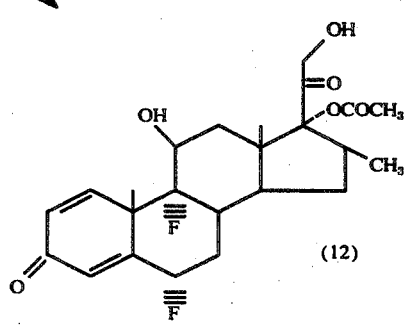
(12)

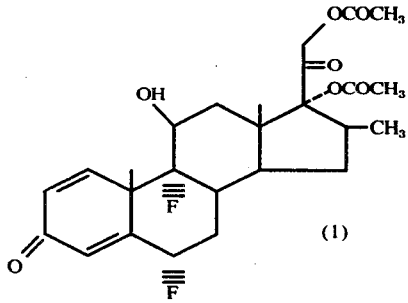

(1)

-continued

In reaction scheme A the starting material, 6α-fluoro-17α,21-dihydroxy-16β-methylpregna-4,9(11)-diene-3,20-dione 21-acetate (2), is disclosed in U.S. Pat. No. 3,557,158 (Example 15A). The conversion of this compound to (3) can be carried out with an acetylating agent such as acetic anhydride or acetic acid in the presence of an acetylation promoter such as trifluoroacetic anhydride and in the presence of a strong acid such as p-toluenesulfonic acid or perchloric acid in a solvent that is inert to the reaction. Alternatively the starting material can be heated under reflux with acetic anhydride and a base such as calcium carbonate for a period of from 3 to 24 hours, then poured into water and worked up in the usual way.

The compounds (3) can be subjected to 1-dehydrogenation at this stage, followed by 9-fluorination, or, alternatively it can be 9-fluorinated and then subjected to 1-dehydrogenation. Both alternative sequences of reaction steps are illustrated in Route A, above, and both produce as a final product the compound of this invention. Which of the two alternative sequences is to be followed is optional and depends upon particular situations of economics, available equipment, reagents, and the like. The general conversion processes involved, i.e., 1-dehydrogenation and 9-fluorination are well known in steroid chemistry and can be carried out as previously applied in the art to similar compounds lacking the 17,21-diacetate groups which characterize this invention. For example, the disclosure and description of these conversion processes in U.S. Pat. No. 3,557,158 are applicable.

The starting material 6α,9α-difluoro-11β,17α,21-trihydroxy-16β-methylpregna-1,4-diene-3,20-dione (10) for Route B is also disclosed in U.S. Pat. No. 3,557,158. The conversion to (11) and then to (12) is carried out in accordance with the processes disclosed in U.S. Pat. No. 3,147,249 and French Pat. 1,332,764. The conversion of (12) to the desired compound (1) involves 21-acetylation and can be carried out in a manner heretofore known to accomplish this with similar steroid compounds, i.e., using acetic anhydride in the presence of a base. The method disclosed in U.S. Pat. No. 3,557,158 is suitable.

An alternate and, in many respects, preferable, method of producing the novel compound (1) through intermediate (7) is schematically shown as follows:

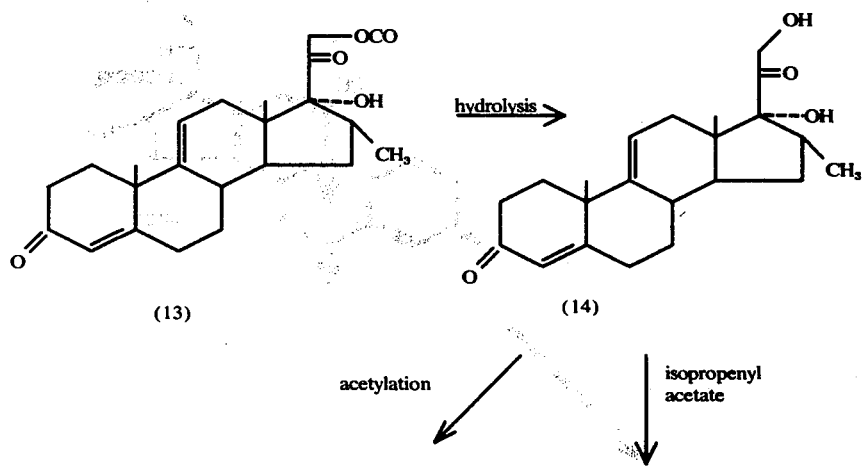

-continued

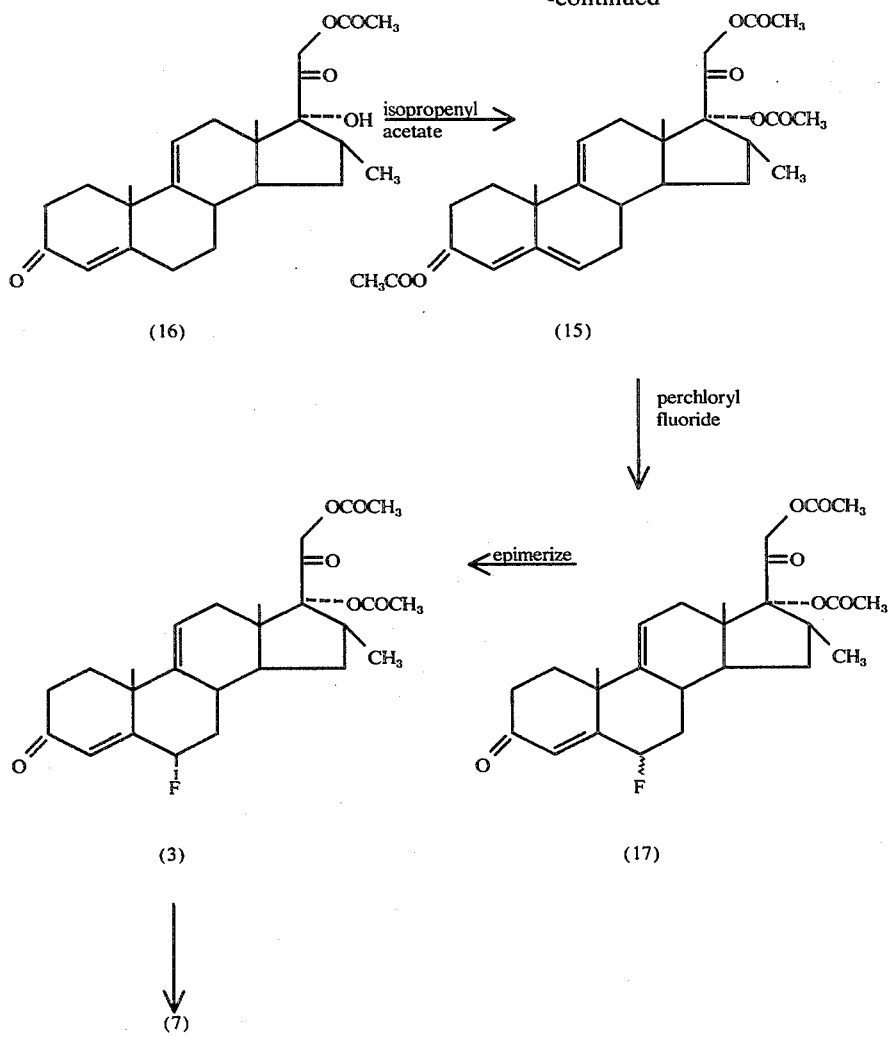

Starting material (13) can be prepared by conventional esterification procedures (applied to the corresponding 21-hydroxy compound) as are used in making analogous steroid 21-benzoates.

The hydrolysis of (13) to (14) can be carried out in known manner as by treatment with a base, e.g. methanolic sodium or potassium carbonate.

The conversion of (14) or (16) to (15) can be carried out in an inert solvent in the presence of an acidic agent such as p-toluenesulfonic acid or phosphoric acid.

The conversion of (15) to (17) can be carried out in solvents such as aqueous dimethylformamide, aqueous acetone, aqueous dioxane, etc. The conversion of (14) to the 21-acetate (16) can be carried out by known 21-acetylation methods, and (16) can be converted like (14) with isopropenyl acetate, to produce (15) as noted above. Alternatively, the direct use of (16) as a starting material is feasible, and these variations are to be considered as optional alternatives to the direct use of (14) to form (17).

The conversion of (17) to (3) is carried out using known epimerizing conditions for converting 6β-fluoro steroids to the corresponding 6α-fluoro steroids, e.g., the use of hydrogen chloride or dimethylformamide (DMF) complex with hydrogen chloride in an inert medium such as chloroform or a mixture of ethanol and chloroform. The starting material (17), made as described above, is a mixture of 6α and 6β epimers, with the latter preponderating.

The foregoing reactions are further illustrated in the Examples which follow.

The steroid (1) can be formulated in a pharmaceutical carrier suitable for application to affected areas of the skin, eyes, ears or mucous membranes to treat inflamed areas. The compositions containing antimicrobial agents find application in the local treatment of infected dermatoses. For example, the antibacterial properties of clindamycin include antibacterial activity against staphylococcal, streptoccal and cornybacteria (c. acnes) infections. The antifungal activity of chloroxide (dichloroxine) includes, for example, antifungal activity against Candida albicans, dermatophytes such as *Tinea capitis* (ring worm of scalp) and *Tinea pedis* (athlete's foot), Chloroxine also exhibits antibacterial activity. Therefore, the combination of the novel anti-inflammatory steroid, clindamycin and chloroxine is useful in treating infected atopic, eczmatoid, stasis, nummular, contact or seborrheic dermatitis, neurodermatitis and dermatitis veneata; infantile eczema; lichen simplex chronicus; pruritus ani and pruritus vulvae. The steroid-antimicrobial compositions are also useful in animal mastitis, a disease of the mammary glands which can be of particular concern in milk-producing animals such as cows.

The term "local" or "topical" as employed here relates to the external use of the medication, incorporated in a suitable base or vehicle, at the site of the inflammation. Accordingly, the compositions of this invention include those pharmaceutical forms in which the medication is applied externally for direct contact with the surface to be treated. Conventional pharmaceutical forms for this purpose include ointments, creams, lotions, solutions, suspensions, pastes, jellies, sprays and aerosols (e.g., for oral or nasal use or on the skin), drops (e.g., for use in the eyes or ears), suppositories (e.g., for rectal or vaginal use), powders (e.g., for use on the skin or for oral or intranasal insufflation), and the like.

Creams are oil-in-water (o/w) or water-in-oil (w/o) emulsions. Pharmaceutically acceptable substances utilized in the emulsions include, for example, water, non-aqueous liquids, semi-solids and emulsifying agents. Ointments are oleoginous preparations in which pharmaceutically acceptable substances include non-emulsion ointment bases. Pastes are usually stiffer, less greasy and more absorptive than ointments, due to a higher proportion of pharmaceutically acceptable powdered ingredients. Lotions are aqueous suspensions, or emulsions or dispersions utilizing pharmaceutically acceptable suspending and emulsifying agents. Powders (dusting powders) are dispensed in a very find state of subdivision and utilize pharmaceutically acceptable carrier powders. Gels are formed by an acidic carboxy polymer and a neutralizing agent. Solutions utilize pharmaceutically acceptable solvents. Aerosols provide very findly subdivided liquid or solid particles after spraying with a pharmaceutically acceptable propellant from an appropriate container.

Examples of non-aqueous liquids include, for example, mineral oil (light and heavy) and olive oil. Semi-solids utilized in creams include, for example, spermaceti, cetyl alcohol, stearic acid, glyceryl monostearate and polyethylene glycol 4000. Emulsifying agents include, for example, acacia, bentonite, polysorbate 80, sodium laural sulfate and calcium oleate. Emulsion bases include, for example, cold cream, hydrophilic ointment and rose water ointment. Non-emulsion ointment bases include, for example, white ointment, yellow ointment, petrolatum, white petrolatum, anhydrous lanolin and hydrophilic petrolatum. Pharmaceutically acceptable powders utilized in pastes include, for example, starch, zinc oxide, calcium carbonate and talc. Pharmaceutically acceptable suspending agents for lotions include, for example, carboxymethylcellulose, acacia, bentonite, and tragacanth. Powders utilized as pharmaceutically acceptable carrier powders include, for example, precipitated calcium carbonate, prepared chalk, magnesium stearate, talc, zinc oxide and zinc stearate. Pharmaceutically acceptable acidic carboxy polymers for gels include, for example, carbonpol 940 and neutralizing agents include, for example, diisopropylamine.

Solvents include, for example, isopropyl alcohol, propylene glycol, polyethylene glycol, various ethers and certain esters. Propellants include, for example, liquified gases such as trichlorofluoromethane (propellant II), dichlorodifluoromethane (propellant 12), chloropentafluoroethane (propellant 115), propane, n-butane, and gases such as nitrogen and carbon dioxide.

Although the topical formulations for use on the skin have a notable anti-inflammatory effect without occlusion, the preparations with the steroid of this invention can also be used effectively with conventional occlusive dressing.

The concentration of the active steroid in the topical formulations can be within the range of 0.001% to 5.0% of the weight of the composition, generally the preferred concentration is in the range of 0.01% to 0.1%.

The concentration of the therapeutically active agents throughout the topical pharmaceutical preparations must be uniform. With lotions shaking before use may be necessary to produce a uniform concentration.

The actual concentration of the therapeutically active agents is adjusted so that an effective amount to produce the desired pharmacological effect will be delivered when a specified amount of the topical pharmaceutical preparation is applied locally. The exact dose depends on the condition of the patient or animal and is easily determined by one skilled in the art.

The topical pharmaceutical preparations are packaged in jars, bottles, tubes, aerosol cans, bottles, boxes as is appropriate for the particular topical preparation and convenient for the patient to use.

The compositions of this invention can also contain other pharmaceutically active ingredients in combination with the active steroid. These other ingredients can be antimicrobial (antibacterial or antifungal) agents such as lincomycin, clindamycin, chlortetracycline, tetracycline, griseofulvin, erythromycin, neomycin, polymyxin, circulin, gramicidin, bacitracin, nystatin, candicidin, nitrofurazone, chlorquinaldol, iodochlorhydroxyquin, diiodohydroxyquin, chloroxine, haloquinol, haloprogin, hexachlorophene, tolnaftate, and the like. Other active ingredients can be keratolytics such as resorcinol, sulfur, salicyclic acid, retinoic acid and the like, antipuritics such as menthol, urea and the like, antihistamines such as chlorocyclizine, tripelennamine, methapyrilene, diphenhydramine, and the like and local anesthetics such as lidocaine, benzocaine and the like. The above pharmaceutically active ingredients are included whether in their free form or present as a pharmaceutically acceptable salt, including internal salts, ester, ester-salt, etc. Examples of the above pharmaceuticals in salt form are neomycin sulfate, polymyxin B sulfate, clindamycin hydrochloride. Clindamycin phosphate is an ester which exists as as internal salt. Clindamycin palmate hydrochloride is an ester-salt.

In those compositions noted above which contain antimicrobial agents, keratolytic agents or antihistaminics, the amount used will be a topically effective amount as is readily determinable by those skilled in the art of formulating antibacterial and antifungal creams and ointments and will, in general, correspond with the amount used to achieve an intermediately potent topical treatment with such known ointments or creams. Further ranges of amounts are listed below, and it is to be understood that the listed ingredients and amounts per gram of topical formulation can be used in any of the topical formulations which are described in the formulation example.

| INGREDIENT | TOPICAL CONCENTRATION | |
|---|---|---|
| | Units of Topical Formulation | Weight/Gram of Topical Formulation |
| Neomycin Sulfate | | 0.5-5.0 mg. |
| Polymyxin B Sulfate | 5,000-10,000 units | |
| Bacitracin | 3,000-5,000 units | |
| Nystatin | 100,000 units | |
| Gramicidin | | 0.1-0.5 mg. |
| Lincomycin | | 10-30 mg. |
| Clindamycin | | 1-50 mg. |
| Chlortetracycline | | 10-30 mg. |
| Tetracycline | | 10-30 mg. |
| Erythromycin | | 10-30 mg. |
| Griseofulvin | | 10-30 mg. |
| Nitrofurazone | | 1-3 mg. |
| Chlorquinaldol | | 10-30 mg. |
| Iodochlorhydroxyquin | | 10-30 mg. |
| Halquinol | | 10-30 mg. |
| Hexachlorophene | | 10-30 mg. |
| Diiodohydroxyquin | | 5-10 mg. |
| Haloprogin | | 5-10 mg. |
| Tolnaftate | | 5-10 mg. |
| Resorcinol | | 5-30 mg. |
| Sulfur | | 10-50 mg. |
| Salicyclic acid | | 10-30 mg. |
| Menthol | | 0.1-1.0 mg. |
| Urea | | 10-50 mg. |
| Circulin | 5,000-10,000 units | |
| Chloroxine | | 10-30 mg. |
| Retinoic acid | | 0.5-10 mg. |
| Candicidin | | 1-25 mg. |
| Chlorcyclizine | | 5-20 mg. |
| Tripelennamine | | 5-20 mg. |
| Methapyrilene | | 5-20 mg. |

The following are preferred general formulations, alternatively plain or containing the above agents in which the strengths in percent relate to the steroid (1).
 a. an 0.2% w/w cream or ointment (higher potency)
 b. an 0.025% w/w cream of ointment (intermediate potency)
 c. An 0.001% w/w cream or ointment (maintenance potency)
 d. an 0.2% w/w cream or ointment (high potency) containing a topically effective amount of one or more antibacterial agents
 e. an 0.025% w/w cream or ointment (intermediate potency) containing a topically effective amount of one or more antibacterial agents
 f. an 0.001% w/w cream or ointment (maintenance potency) containing a topically effective amount of one or more antibacterial agents
 g. an 0.2% w/w cream or ointment (high potency) containing a topically effective amount of one or more antifungal agents
 h. an 0.025% w/w cream or ointment (intermediate potency) containing a topically effective amount of one or more antifungal agents
 i. an 0.001% w/w cream or ointment (maintenance potency) containing a topically effective amount of one or more antifungal agents
 j. an 0.2% w/w cream or ointment (high potency) containing a topically effective amount of a combination of one or more antibacterial agents and one or more antifungal agents
 k. an 0.025% w/w cream or ointment (high potency) containing a topically effective amount of a combination of one or more antibacterial agents and one or more antifungal agents
 l. an 0.001% w/w cream or ointment (high potency) containing a topically effective amount of a combination of one or more antibacterial agents and one or more antifungal agents.

It is preferred that the antibacterial agent when present be clindamycin or pharmaceutically acceptable salt or ester thereof. It is preferred that clindamycin be present as clindamycin hydrochloride at a therapeutically effective amount of about 0.1 percent to 5.0 percent. More preferred is 0.5 percent to 2.0 percent. Most preferred is 1.0 percent.

It is preferred that the antifungal agent when present be chloroxine at a therapeutically effective amount of about 1.0 percent to 3.0 percent. More preferred is 1.0 to 2.0 percent. Most preferred is not more than 1.5 percent.

Specific formulations of the above can be determined readily by reference to the Pharmaceutical Compositions given below.

In general the topical application of the above formulations should be made two to four times daily. The lower formulation can be applied from one to three or four times daily for maintenance.

Parenteral dosage forms of the present invention for intramuscular, subcutaneous, intra-articular and intrabursal use include sterile solutions and suspensions, and sterile powders for the extemporaneous preparation of sterile injectables. In the case of sterile suspensions and powders, it is preferred that the active ingredient be of fine particle size. The solvent or suspending liquid comprises water, vegetable oils, or organic solvents, e.g., glycerol, propylene glycol, polyethylene glycol 400, dimethyl sulfoxide, N,N-dimethylacetamide, 2,2-dimethyl-4-methanol-1,3-dioxolane, isopropyl myristate, 1,3-butanediol, polysorbate 80, ethanol, benzyl alcohol, benzyl benzoate, and the like, or suitable mixtures thereof.

Powders for injectable suspensions are preferably micronized and sterilized by the use of a gas, such as ethylene oxide, after blending with the required additional ingredients in the proper particle size. Just prior to use, the sterile powder is reconstituted in the desired sterile suspending liquid.

The dosage unit forms for parenteral use include single dosage unit products comprising from about 0.2 to about 25 mg. of the principal active ingredient per dosage unit which is administered in suspension or in solution in doses of 1 ml. The multiple dosage unit forms for parenteral use comprise from about 0.01 to about 10 percent weight/ volume of the principal active ingredient.

For oral administration either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or otherwise compounded to provide a dosage form affording the advantage of prolonged or delayed action or predetermined successive action of the enclosed medication. For example, the tablet can comprise an inner dosage and an outer dosage component, the latter being in the form of an envelope over the former.

In their simplest embodiment, capsules, like tablets, are prepared by mixing the active steroid with an inert pharmaceutical diluent and filling the mixture into a hard gelatin gapsule of appropriate size. In another embodiment, capsules are prepared by filling hard gelatin capsules with polymeric acid coated beads containing the principal active material. Soft gelatin capsules are prepared by machine encapsulation of a slurry of the active compound with an acceptable vegetable oil, light liquid petrolatum or other inert oil.

Fluid unit dosage forms for oral administration such as syrups, elixirs, and suspenions can be prepared. An elixir is prepared by using a hydroalcoholic (ethanol) vehicle with sweeteners such as sugar and saccharin, together with an aromatic flavoring agent.

Suspensions can be prepared of the compound of this invention with a syrup vehicle with the aid of a suspending agent such as acacia, tragacanth, methylcellulose and the like.

The dosage unit forms for oral use comprise from about 0.1 to about 15 mg. of the principal active ingredient perdosage unit which is used from 1 to 4 times daily.

The term "dosage unit form" as used in this specification refers to physically discrete units suitable as unitary dosages for human and veterinary subjects, each unit containing a predetermined quantity of active material calculated to produce the desired therapautic effect in association with the required pharmaceutical diluent or carrier. The specifications for the novel dosage unit forms of this invention are dicated by and directly dependent upon (a) the unique characteristics of the active material and the particular therapeutic effect to be achieved and (b) the limitations inherent in the art of compounding such an active material for therapeutic use in human being and in animals, as disclosed in detail in this specification, being features of the present invention. All temperatures are in degrees centigrade.

EXAMPLE 1

6α-fluoro-17α,21-dihydroxy-16β-methylpregna4,9(11)-dione3,20 dione 17,21-diacetate (3)

A solution of 29.86 g. of 6α-fluoro-17α,21-dihydroxy-16β-methylpregna-4,9(11)-diene-3,20-dione 21-acetate (2) in 300 ml. of acetic acid was cooled to 15° with exclusion of moisture. Trifluoroacetic anhydride (120 ml.) was added slowly, maintaining the temperature below 20°, followed by the addition of 3.6 g. of p-toluenesulfonic acid hydrate. The reaction mixture was stirred at 22°–25° for 1.25 hour and then was poured slowly into 3.5 liters of vigorously stirred ice water. The mixture was stirred for an additional 15 min., then filtered to give a pale yellow, pasty product which was transferred to a separatory funnel with 650 ml. of methylene chloride. The organic layer was washed with 375 ml. of 1 N aqueous potassium bicarbonate, filtered through anhydrous sodium sulfate and evaporated to a sticky foam which was redissolved in 175 ml. of boiling methanol. The pale orange solution was conc. to 150 ml., and stirred while being cooled slowly to 5°. The product was collected and dried at 60° in vacuo to give 23.93 g. (72.7%) of (3) as a pale yellow powder, one spot by thin layer chromatography (tlc). A similar preparation had m.p. 190°–195°.

NMR (CDCl$_3$, δ): C-18(0.70), C-19(1.34), 16-CH$_3$ (1.35,J=7), CH$_3$CO-(2.14), -CH$_2$O-(4.85, 4,40,J=16), 11-H (m, centered at 5.68), 4-H(6.12).

EXAMPLE 2

9,11β-epoxy-6α-fluoro-17α,21-dihydroxy-16β-methyl-pregn-4-ene-3,20-dione 17,21-diacetate (5)

A solution of 23.92 g. of (3) in 75 ml. of methylene chloride was diluted with t-butyl alcohol (300 ml.) and 68 ml. of aqueous perchloric acid (10 ml. of 70% perchloric acid diluted to 100 ml.) was added. The solution was cooled to 20°, a solution of N-bromoacetamide (12.1 g.) in 130 ml. of t-butyl alcohol was added and the reaction mixture was kept at about 20° for 0.5 hour, then was cooled to 15° and a solution of sodium sulfite (12.1 g.) was added. The reaction mixture was evaporated to a small volume at reduced pressure, then diluted to 3 liters with ice water. The precipitate was collected, dissolved in 350 ml. of methylene chloride, washed with saturated salt solution, dried and evaporated to give 28.9 g. (100%) of the bromohydrin (4) as a white solid.

A solution of 31.5 g. of (4) in 700 ml. of acetone was stirred and heated under reflux with 35 g. of potassium acetate for 24 hours. The reaction mixture was diluted with 350 ml. of water and evaporated at reduced pressure to give a thick slurry which was diluted to 3 liters with water and cooled to 5°. The precipitate was collected, dissolved in 350 ml. of methylene chloride, washed with saturated salt solution, filtered through anhydrous sodium sulfate and evaporated to give a yellow foam. The foam was crystallized from methylene chloride-methanol and the solids were collected and dried at 60° in vacuo to give 20.89 g. (77.5%) of the epoxide (5) as pale yellow crystals m.p. 215°–216° dec.

NMR (CDCl$_3$, δ): C$_{18}$ (0.86), C$_{19}$ (1.35), 16-CH$_3$ (1.32, J=7), CH$_3$CO-(2.10), 11-H 3,52), —CH$_2$O- (4.34, 4.72, J=16), ½.6-H (5.58-5.88), 4-H (6.03).

EXAMPLE 3

6α,9α-difluoro-11β,17α,21-trihydroxy-16β-methyl-pregn-4-ene-3,20-dione 17,21-diacetate (6)

Tetrahydrofuran (203 g.) was added slowly to anhydrous hydrogen fluoride (113 g.) cooled in a Dry Ice-acetone bath with exclusion of moisture. A solution of 24.34 g. of the epoxide (5) in 100 ml. of chloroform was added and rinsed in with 25 ml. of chloroform. The resultant solution was allowed to stand at −20° for 24 hours and then was poured cautiously into a stirred mixture containing 750 g. of sodium carbonate in 3 liters of water, 3 liters of ice and 2 liters of chloroform. The mixture was stirred for 10 minutes, then the organic layer was filtered through anhydrous sodium sulfate. The aqueous layer was extracted with 500 ml. of chloroform and the combined organic extracts were evaporated at reduced pressure to give (6) as a pale yellow solid.

This material was used in the subsequent DDQ oxidation step (Example 5) without further purification.

EXAMPLE 4

6α,9α-difluoro-11β,17α,21-trihydroxy-16β-methyl-pregn-4-ene-3,20-dione 17,21-diacetate hydrate (6 hydrate)

A sample of (6) prepared as in Example 3 was purified by chromatography on Florisil magnesium silicates. Elution with 22.5% acetone-Skellysolve B hexanes and crystallization of the product-containing fractions successively from methanol and aqueous acetone gave (6) as the hydrate, m.p. 199°–202°.

Analysis:
Calc'd. for $C_{26}H_{34}F_2O_7\cdot H_2O$ (514.55):
C, 60.69; H, 7.05; F, 7.39; $H_2O$, 3.50.
Found: C, 60.97, 61.11; H, 7.24, 6.93, 7.01; F, 7.26; $H_2O$, 3.42.

IR (mineral oil mull, $cm^{-1}$): 3590, 3510, 3310, 1750, 1735, 1725sh, 1690, 1675sh, 1625, 1290, 1245, 1215, 1075, 1035, 875.

UV (95% $C_2H_5OH$): λmax 233 nm (ε16,160). NMR ($CDCl_3$, δ): C-18 (0.97), C-19(1.53), 16-$CH_3$(1.36,J=7), $CH_3CO$-(2.13), -$CH_2O$-(4.36, 4.87, J=17), 11-H(m,centered at 4.36), ½.6-H(m, centered at 5.70), 4-H(6.14).

Anhydrous (6) is obtained by drying a small sample, finely pulverized, at a temperature over 100° and under high vacuum for several days.

EXAMPLE 5

6α,9α-difluoro-11β,17α,21-trihydroxy-16β-methylpregna-1,4-diene-3,20-dione 17,21-diacetate (1)

A solution of (6) (total crude from Example 3) and 13.9 g. of 2,3-dichloro-5,6-dicyano-1,4-benzoquinone (DDQ) in 200 ml. of dioxane was stirred and heated under gentle reflux for 26 hours, additional DDQ (2.3 g.) was then added and heating continued for 15 hours. The reaction mixture was cooled to 15°, then insolubles were collected and washed several times with dioxane. The filtrate was stirred for 1 hour with a solution of 6.5 g. of sodium bisulfite in 60 ml. of water and then was transferred to a separatory funnel with 600 ml. of benzene. Sodium carbonate solution (20%, 65 ml.) was added and the aqueous layer was washed with 300 ml. of benzene.

The organic layer was washed successively with 2 × 150 ml. of 20% aqueous sodium carbonate and 4 × 100 ml. of water, then filtered through anhydrous sodium sulfate and evaporated to give 17.7 g. of a tan foam which was chromatographed on 500 g. of Florisil magnesium silicates. Less polar impurities were eluted with 4.5 liters of 5%, 6 liters of 10% and 6 liters of 15% acetone-Skellysolve B hexanes. Continued elution with 10 liters of 20% acetone-Skellysolve B gave product fractions essentially homogeneous by thin layer chromatography. Successive crystallizations of these fractions from ethyl acetate-Skellysolve B and acetone-methanol gave (1), m.p. 221°–223° dec.

Analysis:
Calc'd. for $C_{26}H_{32}F_2O_7$ (494.52):
C, 63.14; H, 6.52; F, 7.68.
Found: C, 62.89; H, 6.56; F, 7.70.

UV (95% $C_2H_5OH$): λmax 238 nm (ε17,250). NMR ($CDCl_3$, δ): C-18(0.98), C-19(1.53), 16-$CH_3$(1.34, J=7), $CH_3CO$-(2.08, 2.12), -$CH_2O$-(4,78, J=17), 11-H(m, centered at 4.40), ½.6H(m, centered at 5.75), $[\alpha]_D$ ($CHCl_3$) + 61°.

EXAMPLE 6

6α-fluoro-17α,21-dihydroxy-16β-methylpregna-1,4,9(11)-triene-3,20-dione 17,21-diacetate (7)

A sample of 4.6 g. of (3) and DDQ (2.7 g.) in 40 ml. of dry dioxane was stirred for 24 hours at 95°, additional DDQ (0.5 g.) was added and heating was continued for 22 hours. The reaction mixture was then cooled at 15° and filtered. The solids were washed with dioxane and the filtrate was evaporated at reduced pressure in presence of 32 g. of Florisil magnesium silicates. The Florisil containing (7) was transferred to the top of a column of 250 g. of Florisil. Elution with 2.5 liters of 5% and 2.5 liters of 10% acetone-Skellysolve B hexanes removed little material. Continued elution with 5 liters of 15% acetone-Skelysolve B hexanes and combination of fractions pure by tlc gave (7) as a white foam.

NMR($CDCl_3$, δ): C-18(0.74), C-19(1.41), 16-$CH_3$(1.38, J=6), $CH_3CO$-(2.13, 2.17), —$CH_2O$-(4.45, 4.90, J=17), 11-H(m,centered at 5.7), 2-H, 4-H(6.25-6.55), 1-H(7.1-7.4).

EXAMPLE 7

9β,11-epoxy-6α-fluoro-17α,21-dihydroxy-16β-methylpregna-1,4-diene-3,20-dione 17,21-diacetate (9)

A 3 g. sample of (7) was converted to the bromohydrin (8) and thence to the epoxide (9) essentially as described in Example 2. The crude epoxide (2.66 g. of a golden foam) was chromatographed on 125 g. of silica gel. Elution with 2.8 liters of 99:1 methylene chloride/acetone removed less polar impurities. Continued elution with 74:1 methylene chloride/acetone gave fractions containing produce, pure by tlc. Crystallization from methanol gave (9), m.p. 225°–227.5° dec.

NMR($CDCl_3$, δ): C-18(0.87), C-19(1.41), 16-$CH_3$(1.31, J=6), $CH_3CO$-(2.10), 11-H(3.32). —$CH_2O$-(4.33, 4.71, J=16), ½.6-H(m, centered at 5.8), 1-H 2-H, 4-H(6.0-6.7).

EXAMPLE 8

6α,9α-difluoro-11β,17α,21-trihydroxyl-16βmethylpregna-1,4-diene-3,20-dione 17,21-deacetate (1)

A sample of (9) was treated with hydrogen flurodie/tetrahydrofuran in the same manner as in Example 3. Two crystallizations from methanol gave a sample, m.p. 217°–219° dec., containing only trace impurities by tlc. Repeated chromatography and recrystallizations affords (1), essentially free of impurities.

EXAMPLE 9

6α,9α-dilfuoro-11β,17α,21-trihydroxyl-16β-methylpregna-1,4-diene-3,20-dione 17,21-methyl orthoacetate (11) ..

A solution of 12.38 g. of 6α,9α-difluoro-11β,17α,21-trihydroxy-16β-methylpregna-1,4-diene-3,20-dione (10) in 20 ml. of dimethylformamide was diluted with 360 ml. of benzene, p-toluenesulfonic acid hydrate (66 mg.) was added and the mixture was heated to boiling. After 10 ml. of distillate was collected, trimethylorthoacetate (10 ml.) was added and rapid distillation was continued. After 30 min. (175 ml. of distillate), additional p-toluenesulfonic acid hydrate (24 mg.) was added. The reaction was continued for 10 min. (215 ml. of distillate), then the solution was cooled under $N_2$ and triethylamine (0.2 ml.) was added. The reaction mixture was transferred to a separatory funnel with benzene, washed with 3×100 ml. 1 N potassium bicarbonate and 1×100 ml. saturated salt solution, then filtered through anhydrous sodium sulfate and evaporated to give (11) as a white solid which was used directly in the next step.

EXAMPLE 10

6α,9α-difluoro-11β,17α,21-trihydroxyl-16β-methyl-pregna-1,4-diene-3,20-dione 17-acetone (12)

A solution of crude 811) from Example 9 in 700 ml. of hot methanol was cooled to 25° and there was added 140 ml. of pH 3 buffer of 5 volumes of aqueous potassium hydrogen phthalate (0.05 M) mixed with 1 volume of 0.10 N hydrochloric acid. The solution was allowed to stand at room temperature under a $N_2$ atmosphere for 24 hours and then was stirred and diluted slowly with 520 ml. of water. After cooling to 10°, the product was collected, washed with water and dried at 80° to give (12), homogeneous by tlc.

EXAMPLE 11

6α,9α-difluoro-11β,17α,21-trihydroxy-16β-methyl-pregna-1,4-diene-3,20-dione 17,21-diacetate (1)

A 5.50 g. sample of (12) dissolved in pyridine (5 ml.) and acetic anhydride (10 ml.) was allowed to stand at 5° for 30 hours, then was diluted with 10 ml. of acetone and cooled to 10°. Water (100 ml.) was added very slowly with efficient stirring.

After cooling for 6 hours at 5° the precipitate was collected, washed with water and dried at 60° in vacuo to give (1). Traces of impurities are removed, if desired, by chromatography and recrystallization as described in Example 5.

EXAMPLE 12

17α,21-dihydroxy-16β-methylpregna-4,9(11)-diene-3,20-dione 21-benzoate (13).

A solution of 13 g. of pyridine sulfur trioxide complex in 50 ml. of dimethylsulfoxide is added dropwise over a period of about 6 min. to a vigorously stirred mixture of 7.0 g. of 17α,20α,21-trihydroxy-16β-methyl 4,9(11)-pregnadien-3-one 21-benzoate (see Example 13 of U.S. application Ser. No. 137,051, filed Apr. 23, 1971) in 37 ml. of dimethylsulfoxide and 34 ml. of triethylamine, while keeping the temperature at about 20° C. The resulting mixture is then stirred at room temperature for about 1 hr. The pH of the mixture is adjusted to 4.5 by the addition of 18% aq. HCl. The mixture is then diluted with water and filtered. The solids thus obtained are washed with water and dried under vacuum to give 6.95 g. of partially oxidized product. The product (6.95 g.) thus obtained is oxidized again using the same procedure as above to give 6.9 g. of material, which is triturated with 30 ml. of methanol to give 5.70 g. (81.7% yield) of oxidized product. The product thus obtained is crystallized from methanol to give 4.7 g. of 17α,21-dihydroxy-16β-methylpregna-4,9(11)- diene-3,20-dione 21-benzoate (13), m.p. 198.5°–203.5° C.; $[\alpha]_D$ +167° ($CHCl_3$).

Following the procedure of Example 12, above, but substituting 17α,20β,21-trihydroxy-16β-methylpregna-4,9(11)-diene-3-one 21-benzoate as starting material in place of the corresponding 20α-isomer, 17α,21-dihydroxy-dihydroxy-16β-methylpregna-4,9(11)-diene-3,20-dione 21-benzoate (13) is obtained.

EXAMPLE 13

17α,21-dihydroxy-16β-methylpreg-4,9(11)-diene-3,20-dione (14).

A solution of 18.4 g. of 17α,21-dihydroxy-16β-methylpregna-4,9(11)-diene-3,20-dione 21-benzoate (13) in 400 ml. of boiling methanol was cooled under nitrogen to 32°, and potassium carbonate (3.04 g.) in 30 ml. of water was added. The reaction mixture was stirred for 1.5 hours at 26°–30°, then the yellow solution was acidified with acetic acid. Water (100 ml.) was added slowly, then methanol was evaporated (bath 30°–40°) at reduced pressure with concurrent addition of 170 ml. of water to a final volume of about 370 ml. The mixture was then stirred in an ice bath for 45 min., the precipitate collected and dried at 60α in vacuo to give 14.12 g. (99%) of (14), m.p. 167°–168°.

EXAMPLE 14

17α,21-dihydroxy-16β-methylpregna-4,9(11)-diene-3,20-dione 21 acetate (16).

The 17,21-diol (14) (14.12 g.) was stirred with pyridine (20 ml.) and acetic anhydride (40 ml.) for 5 hours. The reaction mixture was cooled in an ice bath, then diluted slowly with water to 500 ml. and the product isolated and dried at 80° in vacuo to give 15.31 g. (97%) of (16). A sample of (16) was crystallized several times from acetone-Skellysolve B hexanes to give an analytical sample, m.p. 209.5°–216°, $[\alpha]_D$ +136° (C 0.91 $CHCl_3$), λmax 239 nm ($\epsilon$ 17,450).

EXAMPLE 15

3,17α,21-trihydroxy-16β-methylpregna-3,5,9-(11)-trien-20-one 3,17,21-triacetate (15).

A mixture of 11 g. of (16), 275 ml. of benzene and 137 ml. of isopropenyl acetate containing 0.4 ml. of 85% phosphoric acid was heated under reflux for 2 hours. The reaction mixture was then cooled, treated with triethylamine (1 ml.) and then evaporated to dryness at reduced pressure to give (15) as a gray oil which slowly crystallized upon standing. A portion was chromatographed on silica gel and crystalline (15) was eluted with 50:1 methylene chloride-acetone.

NMR ($CDCl_3$, δ): $C_{18}$ (0.70), C-19 (1.17), 16-$CH_3$ (1.36, J=7), $CH_3CO$- (2.17), -$CH_2O$- (4.43, 4.85, J=16), 4-H, 6-H, 11-H (5.3–5.9).

The triacetate (15) is also obtained when the 17,21-diol (14) is treated in the manner described above.

EXAMPLE 16

6α-fluoro-17α,21-dihydroxy-16β-methylpregna-4,9(11)-diene-3,20-dione 17,21-diacetate (3).

A 13.3 g. sample of (5) was dissolved in 200 ml. of dimethylformamide and diluted with 30 ml. of water. A slow stream of perchloryl fluoride was introduced into the stirred solution maintaining the temperature at about 30° and the acidity at about pH4 by concurrent addition of 10% aqueous sodium hydroxide. When the starting material was consumed, the reaction mixture was purged with a steam of nitrogen and then was diluted with benzene. The benzene extract was washed thoroughly with water, dried over magnesium sulfate and evaporated to give 14 g. of a yellow foam consisting mainly of a mixture of (3) and the corresponding 6β-fluoro isomer. To equilibrate the mixture of 6-fluoro isomers (17) and a produce a higher proportion of the desired (3), the total reaction mixture was dissolved in 40 ml. of chloroform and treated with 0.60 g. of dimethylformamide hydrogen chloride complex. The solution was allowed to stand for about 18 hours at ambient temperature and then was diluted with methylene chloride and washed with dilute aqueous potassium bicarbonate. The organic extract was dried over magnesium sulfate and evaporated to give 13.8 g. of a brown foam which was chromatographed on Florisil packed in methylene chloride. Elution with increasing concentrations of acetone in methylene chloride gave fractions containing only 6α-fluoro isomer by tlc analysis. These fractions were combined and crystallized from methanol to give (3), m.p. 190°–192° dec.

UV (95% $C_2H_5O_{11}$): λmax 234 nm (ε 17,100). IR (mineral oil mull, $cm^{-1}$): 1755, 1725, 1680, 1620, 1250, 1235, 1235, 1200, 1075, 975 and 875.

Anal. Calc'd. for $C_{25}H_{33}FO_8$ (460.52): F, 4.13. Found: F, 4.47.

Compound (3) is identical in all respects with the compound of Example 1.

PHARMACEUTICAL COMPOSITIONS

The novel compound of this invention (1) can be formulated as follows.

EXAMPLE A

Water-washable cream

The following ingredients are formulated:

| Ingredients | Per Cent w/w |
|---|---|
| 6α,9α-difluoro-11β, 17α,21-trihydroxy-16β-methylpregna-1,4-diene-3,20-dione 17,21-diacetate (1) | 0.025 |
| Mineral Oil | 6.0 |
| Petrolatum | 15.0 |
| Polyethylene glycol 1000 monocetyl ether | 1.8 |
| Cetostearyl alcohol | 7.2 |
| Chlorocresol | 0.1 |
| Distilled water to produce 100 parts by weight | |

The steroid (1) is ball-milled with a little mineral oil to a particle size of less than 5 microns. The water is heated to boiling, he chlorocresol added and the solution then cooled to 65° C. Then the petrolatum, cetostearyl alcohol and polyethylene glycol ether are mixed together while heating to 65° C. The milled steroid suspension is then added to the melt rinsing the container with mineral oil. The steroid oily phase thus prepared is added at 60° C. to the chlorocresol aqueous phase at 65° C. The mixture is stirred rapidly while cooling past the gelling point (40° – 45° C.) and the stirring is continued at a speed sufficiently slow to permit the cream to set.

The water-washable cream is used in the treatment of the majority of steroid-responsive dermatoses using either the open (without occlusion) or occlusive method of drug application.

A small amount of cream is applied to the affected skin area two or three times a day as needed for the treatment of atopic dermatitis, neurodermatitis, contact dermatitis, *seborrheic dermatitis, eczematous dermatitis, pruritis ani, intertrigo, intertriginous psoriasis* and the like.

The quantity of steroid can be increased to 0.2 percent w/w to achieve a higher potency cream or decreased to 0.01 or 0.001 percent w/w to achieve a lower potency maintenance cream.

EXAMPLE A1

Water-washable cream

The following ingredients are formulated:

| Ingredients | Per Cent w/w |
|---|---|
| 6α,9α-difluoro-11β,17α,21-trihydroxy-16β-methyl-pregna-1,4-diene-3,20-dione 17,21-diacetate (1) | 0.05 |
| Stearic Acid | 10.0 |
| Sorbitan Monostearate | 5.0 |
| Sorbitan Monooleate | 1.0 |
| Polyoxyethylene sorbitan monostearate | 2.6 |
| Citric Acid | 0.01 |
| Sorbic acid | 0.2 |
| Propylene Glycol | 15.0 |
| Distilled water to produce 100 parts by weight. | |

The ingredients are formulated as in Example A.

EXAMPLE A2

The ingredients above plus 3.0 weight percent of Halquinol in addition is formulated as above to provide a water washable cream containing an antimicrobial preparation.

EXAMPLE A3

The same ingredients as in the Example A1 with the addition of 0.5% w/w of neomycin sulfate was formulated as in the Example A to provide a water washable cream containing an antibiotic.

EXAMPLE A4

The same ingredients as in the Example A1 with the addition of 0.5% w/w of neomycin sulfate and 3.0% w/w of Halquinol was formulated as in Example A1 to provide a water washable cream.

EXAMPLE 5

The same ingredients as in Example A1 with the addition of 100,000 units of nystatin sulfate and 10 mg. of tolnaftate was formulated as in Example A1 to provide a water washable cream.

EXAMPLE B

Water-washable cream

The following ingredients are formulated:

| Ingredients | Per Cent w/w |
|---|---|
| 6α,9α-difluoro-11β,17α, 21-trihydroxy-16β-methyl-pregna-1,4-diene-3,20-dione 17,21-diacetate (1) | 0.025 |
| Stearic acid | 10.0 |
| Sorbitan monostearate | 5.2 |
| Sorbitan monooleate | 1.0 |
| Polyoxyethylene sorbitan monostearate | 2.8 |
| Citric acid | 0.01 |
| Sorbic acid | 0.20 |
| Propylene glycol | 5.0 |
| Distilled water to produce 100 parts by weight. | |

A mixture of the stearic acid, sorbitan monooleate, sorbitan monostearate, poloxyethylene sorbitan monostearate is heated to 60°–65° C. and added to a stirred solution containing citric acid and sorbic acid dissolved in the water at 60°–65° C. The mixture is stirred at 60°–65° C. and a solution of the steroid (1) in the propylene glycol is added after cooling to 50° C.

The quantity of steroid can be increased to 0.2 percent w/w to achieve a higher potency cream or decreased to 0.01 or 0.001 percent w/w to achieve a lower potency maintenance cream.

EXAMPLE C

OINTMENT

The following ingredients are formulated:

| Ingredients | Per Cent w/w |
|---|---|
| 6α,9α-difluoro-11β,17α,21-trihydroxy-16β-methyl-pregna-1,4-diene-3,20-dione 17,21-diacetate (1) | 0.025 |
| Mineral oil | 10.0 |
| Petrolatum to produce 100 parts by weight. | |

The steroid is ball-milled in a little of the mineral oil to a particle size preferably mostly below 2 microns. The resulting paste is diluted and rinsed from the mill with the remaining mineral oil and made into a suspension by thorough mixing. The suspension is added to the milled petrolatum at 50° C. The mixture is stirred while cooling to produce a homogeneous ointment.

A small amount of this ointment is applied to the affected area two or three times a day as needed for the relief of atopic dermatitis.

The quantity of steroid can be increased to 0.2 percent w/w to achieve a higher ointment or decreased to 0.01 to 0.001 percent w/w to achieve a lower potency maintenance ointment.

EXAMPLE 1

Ointment

The following ingredients are formulated:

| Ingredients | Per Cent w/w |
|---|---|
| 6α,9α-difluoro-11β,17α,21-trihydroxy-16β-methyl-pregna-1,4-diene-3,20-dione 17,21-diacetate (1) | 0.025 |
| Mineral oil | 10.0 |
| Neomycin Sulfate | 0.05 |
| Petrolatum to produce 100 parts by weight. | |

The steroid and neomycin sulfate are ball-milled in a little of the mineral oil to a particle size preferably mostly below 2 microns. The resulting paste is diluted and rinsed from the mill with the remaining mineral oil and made into a suspension by thorough mixing. The suspension is added to the milled petrolatum at 50° C. The mixture is stirred while cooling to produce a homogeneous ointment.

A small amount of this ointment is applied to the affected area two or three times a day as needed for the relief of atopic dermatitis.

The quantity of steroid can be increased to 0.2 percent w/w to achieve a higher potency ointment or decreased to 0.01 or 0.001 percent w/w to achieve a lower potency maintenance ointment.

EXAMPLE D

Ointment

The following ingredients are formulated:

| Ingredients | Per Cent w/w |
|---|---|
| 6α,9α-difluoro-11β,17α,21-trihydroxy-16β-methyl-pregna-1,4-diene-3,20-dione 17,21-diacetate (1) | 0.025 |
| Wool Fat | 4.0 |
| Propylene Glycol | 5.0 |
| Petrolatum to produce 100 parts by weight. | |

A mixture of the wool fat and petrolatum is heated to 60°–65° C. and to the heated mixture is added a solution of the active steroid in propylene glycol, heated to 60°–65° C. The resulting total mixture is stirred while permitting it to cool to room temperature to form a homogeneous ointment.

This formulation is applied primarily without occlusion in the treatment of dry, scaly, ichthyotic-type inflammatory dermatoses where the emollient properties of the ointment are beneficial and where occlusive dressings ordinarily have been used.

EXAMPLE D1

Ointment

The following ingredients are formulated:

| Ingredients | Per Cent w/w |
|---|---|
| 6α,9α-difluoro-11β,17α,21-trihydroxy-16β-methyl-pregna-1,4-diene-3,20-dione 17,21-diacetate (1) | 0.025 |
| Neomycin Sulfate | 0.05 |
| Wool Fat | 4.0 |
| Propylene Glycol | 5.0 |
| Petrolatum to produce 100 parts by weight. | |

A mixture of the wool fat and petrolatum is heated to 60°–65° C. and to the heated mixture is added a solution of the active steroid and the neomycin sulfate in propylene glycol, heated to 60°–65° C. The resulting total mixture is stirred while permitting it to cool to room temperature to form a homogeneous ointment.

This formulation is applied primarily without occlusion in the treatment of dry, scaly, ichthyotic-type inflammatory dermatoses where the emollient properties of the ointment are beneficial and where occlusive dressings ordinarily have been used.

EXAMPLE E

Ointment

The formulation given in Example D and D1 are made up except that the propylene glycol is replaced by an equal amount of butane-2,3-diol.

EXAMPLE F

Lotion (oil-in-water type)

The following illustrates the preparation of 20 liters of a standard lotion:

| Each ml contains | | | |
|---|---|---|---|
| 1 mg. | 6α,9α-difluoro-11β,17α,21-trihydroxy-16β-methylpregna-1,4-diene-3,20-dione 17,21-diacetate (1) | 20 gm. |
| 2 mg. | Methylparaben | 40 gm. |
| 3 mg. | n-Butyl-p-hydroxybenzoate | 60 gm. |
| 0.1 mg. | Citric acid | 2 gm. |
| 25 mg. | Propylene glycol | 500 gm. |

-continued

| Each ml contains | | |
|---|---|---|
| 20 mg. | Polysorbate 80 | 400 gm. |
| 25 mg. | Glyceryl monostearate-diethylaminoethyl oleyl amide phosphate* | 500 gm. |
| 10 mg. | Spermaceti | 200 gm. |
| | Deionized water q.s.a.d. 20 liters | |

*Tegacid regular (Goldschmidt Co.)

The methylparaben, n-butyl-p-hydroxybenzoate, citric acid and steroid are dissolved in propylene glycol. To 9 liters of deionized water heated to from 70° to 80° C. is added the propylene glycol solution, polysorbate 80 glyceryl monostearate-diethylamino ethyl oleyl amide phosphate and spermaceti. The temperature of the mixture is maintained at from 70° to 80° C. for 30 minutes and then allowed to cool spontaneously to from 35° to 45° C. Sufficient water to make 20 liters is added and the mixture stirred, strained, and put through a homogenizer. After homogenization, the lotion is stirred slowly to remove any entrapped air and then placed in suitable containers.

This lotion is useful in treating certain inflammatory dermatoses such as contact dermatitis, chronic eczematous dermatitis, seborrheic dermatitis, otitis external, atopic dermatitis and intertriginous psoriasis.

EXAMPLE G

Ointment

The formulation given in Example D and D1 are made up except that the propylene glycol is replaced by an equal amount of 1,3-butanediol.

EXAMPLE H

Ointment

The formulation given in Example D and D1 are made up except that the amount of steroid (1) is reduced to 0.01%.

The following examples illustrate the preparation of suitable solutions for local or topical anti-inflammatory uses such as:

EXAMPLE I

Solution

The following formualtion is made up

| Ingredients | Per Cent w/w |
|---|---|
| 6α,9α-difluoro-11β,17α,21-trihydroxy-16β-methyl-pregna-1,4-diene-3,20-dione 17,21-diacetate (1) | 0.01 |
| 2,3-butanediol | 99.98 |
| Citric Acid | 0.01 |

The steroid (1) is stirred with a solution of the citric acid in 2,3-butanediol until a clear solution is obtained at room temperature.

The solution is particularly useful for treating lesions in hairy or intertriginous areas such as the scalp, external ear, axillary, inguinal and interdigital sites to relieve such conditions as seborrheic dermatitis, chronic eczematous dermatitis, otitis external, anogenital dermatitis, contact dermatitis, sweat retention syndromes, intertriginous psoriasis, and the like.

EXAMPLE J

Solution

The same formulation as that shown in Example I was made up except that the 2,3-butanediol is replaced by an equal amount of propylene glycol.

EXAMPLE K

Solution

The same formulation given in Example I is made up except that the 2,3-butanediol is replaced by an equal amount of 1,3-butanediol.

EXAMPLE L

Solution

The same formulation given in Example I is made up except that the 2,3-butanediol is replaced by an equal amount of 95% ethyl alcohol. The citric acid can be left out of this preparation as well as the others and still have a useful product.

EXAMPLE M

Eye-ear drops

A sterile vehicle is prepared from the following types and amounts of ingredients using conventional pharmaceutical techniques:

| Each ml. | | |
|---|---|---|
| 4.5 mg. | Sodium citrate | 49.5 gm. |
| 120 mg. | Polyethylene glycol 4000 | 1320 gm. |
| 0.2 mg. | Myristyl-gamma-picolinium chloride | 2.2 gm. |
| 1 mg. | Polyvinylpyrrolidone | 11 gm. |
| | Sodium hydroxide reatent, to pH 7 to 7.4 | |
| q.s. | Water for injection q.s.a.d. | 11,000 ml. |

Ths sterilized micronized active steroid (1) is added to the above vehicle, in the amount of 11 gm. to provide a final concentration of 0.1 percent by weight.

As a complementary active ingredient, sterilized neomycin sulfate can be added in the amount of 55 gm. to provide a final concentration of 0.5 percent by weight.

The compositions are filled into 5 ml. bottles, under techniques designed to guarantee sterility, and used in the treatment of ocular and external ear inflammation.

EXAMPLE N

Suppository, rectal

One thousand suppositories each weighing 2.5 gm. and containing 1 mg. of micronized active steroid can be prepared from the following types and amounts of ingredients:

| Polymyxin B sulfate (10,000 units/mg.) | 1.25 | gm. |
|---|---|---|
| Benzocaine | 75 | gm. |
| Zinc oxide | 62.5 | gm. |
| Propylene glycol | 162.5 | gm. |
| Polyethylene glycol 4000 q.s. | 2500 | gm. |

The active steroid (1), polymyxin B sulfate, benzocaine and zinc oxide are added to the propylene glycol and the mixture milled until a uniform dispersion is produced. The polyethylene glycol 4000 is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally for local treatment of inflammation and infection and anogenital pruritis.

EXAMPLE O

Mastitis ointment

One thousand gm. of an ointment for the treatment of mastitis in dairy cattle is prepared from the following types and amounts of ingredients:

| | | |
|---|---|---|
| 6α,9α-difluoro-11β,17α,21-trihydroxy-16β-methyl-pregna-1,4-diene-3,20-dione 17,21-diacetate (1) | 0.25 | gm. |
| Mineral oil | 300 | gm. |
| Chlorobutanol, anhydrous | 5 | gm. |
| Polysorbate 80 | 5 | gm. |
| 2% Aluminum monostearate-peanut oil gel | 400 | gm. |
| Petrolatum q.s. | 1000 | gm. |

The steroid is milled with the mineral oil until uniformly dispersed. The chlorobutanol, polysorbate 80, peanut oil gel and petrolatum are heated to 120° F. to form a melt and the mineral oil dispersion stirred in. With continued stirring the dispersion is allowed to cool (and congeal) to room temperature and is filled into disposable mastitis syringes in 10 gm. doses.

EXAMPLE P

Troches

Ten thousand troches can be prepared from the following types and amounts of ingredients:

| | | |
|---|---|---|
| 6α,9α-difluoro-11β,17α,21-trihydroxy-16β-methyl-pregna-1,4-diene-3,20-dione 17,21-diacetate (1) | 0.50 | gm. |
| Neomycin sulfate | 50 | gm. |
| Polymyxin B sulfate (10,000 units/mg.) | 1 | gm. |
| Benzocaine | 50 | gm. |
| Calcium stearate | 150 | gm. |
| Powdered sucrose q.s. | 5000 | gm. |

The powdered materials are mixed thoroughly and then compressed into half gram troches following the usual techniques for the preparation of compressed tablets.

The troches are held in the mouth and allowed to dissolve slowly to provide treatment for inflammation in the mouth.

EXAMPLE Q

Aqueous Suspension for Injection

A suspending vehicle is prepared from the following materials:

| | | |
|---|---|---|
| Polyethylene glycol 4000 | 30 | gm. |
| Potassium chloride | 11.2 | gm. |
| Polysorbate 80 | 2 | gm. |
| Methylparaben | 1.8 | gm. |
| Propylparaben | 0.2 | gm. |

-continued

| | | |
|---|---|---|
| Water for injection q.s. | 1000 | ml. |

The parabens are added to a major portion of the water and are dissolved therein by stirring and heating to 65° C. The resulting solution is cooled to room temperature and the remainder of the ingredients are added and dissolved. The balance of the water to make up the required volume is then added and the solution sterilized by filtration. The sterile vehicle thus prepared is then mixed with 5 gm. of the active steroid (1) which has been previously reduced to a particle size less than about 10 microns and sterilized with ethylene oxide gas. The mixture is passed through a sterilized colloid mill and filled under aseptic conditions into sterile containers which are then sealed.

Each milliliter of this suspension contains 5 mg. of active steroid and is administered intramuscularly in 1 ml. doses to alleviate arthritic pain and to produce prolonged relief from joint inflammation.

EXAMPLE R

Oral Tablets 10,000 tablets for oral administration can be prepared from the following types and amounts of ingredients. Each tablet contains 0.5 mg. of active steroid.

| | | |
|---|---|---|
| 6α,9α-difluoro-11β,17α,21-trihydroxy-16β-methyl-pregna-1,4-diene-3,20-dione 17,21-diacetate (1) | 5 | gm. |
| Lactose | 1600 | gm. |

The finely powdered active ingredient and lactose are mixed well and granulated with syrup-starch paste. Starch, talc and calicum stearate are used as lubricants in the compressing step.

The tablets are useful in the systemic treatment of rheumatoid arthritis, allergic dermatoses, atopic dermatitis, eczematoid dermatitis, asthma, serum sickness, drug sensitivity, bursitis, synovitis, tenoynovitis, optic neuritis and acute rheumatic fever.

EXAMPLE S

Oral Aqueous Suspension

An aqueous suspension for oral administration, containing in each teaspoonful (approximately 5 ml.) 0.5 mg. of active steroid is prepared from the following types and amounts of ingredients:

| | | |
|---|---|---|
| 6α,9α-difluoro-11β,17α,21-trihydroxy-16β-methyl-pregna-1,4-diene-3,20-dione 17,21-diacetate (1) | 0.1 | gm. |
| Preservative | 2 | gm. |
| Flavor, q.s. | | |
| Purified water USP, q.s. | 1000 | gm. |

The preservative and flavor are dissolved in the water. The micronized active ingredient is added and the whole is homogenized.

EXAMPLE T

Oral Gelatin capsules 1,000 gelatin capsules for oral administration, each containing 0.24 mg. of active steroid can be prepared from the following types and amounts of materials:

| | | |
|---|---|---|
| 6α,9α-difluoro-11β,17α,21-trihydroxy-16β-methyl-pregna-1,4-diene-3,20-dione 17,21-diacetate (1) | 0.25 | gm. |
| Vegetable oil, q.s. | | |

The micronized active ingredient and the oil are mixed and the mix is encapsulated by the usual techniques into gelatin capsules.

Example U

| | | |
|---|---|---|
| 6α,9α-difluoro-11β,17α,21-trihydroxy-16β-methyl-pregna-1,4-diene-3,20-dione 17,21-diacetate (1) | 0.05 | gm. |
| Liquid dimethylpolysiloxane | 25.0 | ml. |
| Isopropanol | 22.0 | ml. |
| Carboxypolymethylene polymer* | 0.75 | gm. |
| Diisopropanolamine | 0.75 | gm. |
| Distilled water q.s.a.d. | 100.0 | gm. |

*Carbopol 940 (B. F. Goodrich Co.)

Dissolved the active steroid in the isopropanol. Combine this with the water. Add the carboxypolymethylene polymer and stir until uniform. Add the the diisopropanolamine and stir until a smooth gel is obtained. While stirring, add the liquid dimethylpolysiloxane slowly and mix until uniform. This cream-like material is suitable for topical anti-inflammatory applications.

Example V

| Topical Cream | | |
|---|---|---|
| Part I | | |
| 6α,9α-difluoro-11β,17α,21-trihydroxy-16β-methyl-pregna-1,4-diene-3,20-dione 17,21-diacetate (1) | 0.05 | gm. |
| Clindamycin hydrochloride | 1.00 | gm. |
| Chloroxine | 1.00 | gm. |
| Propylene glycol | 15.00 | gm. |
| Part II | | |
| Stearic Acid | 9.16 | gm. |
| Sorbitan monostearate | 4.76 | gm. |
| Sorbitan monooleate | 0.92 | gm. |
| Polysorbate 60 | 2.56 | gm. |
| Part III | | |
| Sodium EDTA | 0.10 | gm. |
| Purified water USP q.s.a.d. | 100.00 | gm. |

In separate containers, heat Part I to 55° C., Part II to 65° C., and Part III to 65° C. and mix each part well. Add Part II to Part III with stirring and mix well, then add Part I. Cool to 50° C. and homogenize.

EXAMPLE W

Topical Cream

Following the procedure of Example V but omitting chloroxine there is produced a topical cream containing the anti-inflammatory steroid 6α,9α-difluoro-11β, 17α,21-trihydroxy-16β-methylpregna-1,4-diene-3,20-dione 17, 21-diacetate and the antibacterial agent clindamycin.

Example X

| Topical Ointment | | |
|---|---|---|
| 6α,9α-difluoro-11β,17α,21-trihydroxy-16βmethyl-pregna-1,4-diene-3,20-dione 17,21-diacetate (1) | 0.05 | gm. |
| Clindamycin | 1.00 | gm. |
| Chloroxine | 1.00 | gm. |
| Propylene Glycol | 7.00 | gm. |
| Glyceryl monostearate with emulsifier | 5.00 | gm. |
| White petrolatum q.s.a.d. | 100.00 | gm. |

Heat the propylene glycol to 55° C. Add 6α,9α-difluoro-11β,17α,21-trihydroxy-16β-methylpregna-1,4-diene-3,20-dione 17,21-diacetate, clindamycin, chloroxine and mix well. Add the remaining ingredients and mix until melted. Remove from heat and mix slowly until cooled to 45° C., then homogenize.

EXAMPLE Y

Topical Ointment

Following the procedure of Example X but omitting the chloroxine there is produced a topical ointment containing the anti-inflammatory steroid 6α,9α-difluoro-11β,17α,21-trihydroxy-16β-methylpregna-1,4-diene-3,20-dione 17,21-diacetate and the antibacterial agent clindamycin.

We claim:

1. A therapeutic composition for topical or local application for treatment of affected dermatosis comprising an anti-inflammatory therapeutic amount of 6α,9α-difluoro-11β, 17α,21-trihydroxy-16β-methyl-pregna-1,4-diene-3,20-dione 17,21-diacetate, an antibacterial therapeutic amount of clindamycin or pharmaceutically acceptable salt or ester thereof and an antifungal therapeutic amount of chloroxine in association with a pharmaceutical carrier.

2. A therapeutic composition according to claim 1, where the anti-inflammatory therapeutic amount of 6α,9α-difluoro-11β, 17α,21-trihydroxy-16β-methyl-pregna-1,4-diene-3,20-dione 17,21-diacetate is from about 0.01 percent to about 0.1 percent, where the antibacterial therapeutic amount of clindamycin or a pharmaceutically acceptable salt or ester thereof is from about 0.5 percent to about 2 percent and where the antifungal therapeutic amount of chloroxine is from about 1 percent to about 2 percent.

3. A therapeutic composition according to claim 1 where the anti-inflammatory therapeutic amount of 6α,9α-difluoro-11β, 17α,21-trihydroxy-16β-methyl-pregna-1,4-diene-3,20-dione 17,21-diacetate is 0.05 percent, where the antibacterial therapeutic amount of clindamycin or a pharmaceutically acceptable salt or ester thereof is 1 percent and where the antifungal therapeutic amount of chloroxine is not more than 1.5 percent.

4. A therapeutic composition according to claim 3 which is a cream.

5. The therapeutic composition according to claim 3 which is an ointment.

6. A therapeutic composition for topical or local application for treatment of infected dermatoses comprising an anti-inflammatory therapeutic amount of 6α,9α-difluoro-11β, 17α,21-trihydroxy-16β-methyl-pregna-1,4-diene-3,20-dione 17,21-diacetate and an antibacterial therapeutic amount of clindamycin or a pharmaceutically acceptable salt or ester thereof in association with a pharmaceutical carrier.

7. A therapeutic composition according to claim 6 where the anti-inflammatory therapeutic amount of 6α,9α-difluoro-11β, 17α,21-trihydroxy-16β-methyl-pregna-1,4-diene 3,20-dione 17,21-diacetate is from about 0.01 percent to about 0.1 percent and the antibacterial therapeutic amount of clindamycin or a pharmaceutically acceptable salt or ester thereof is from about 0.5 percent to about 2 percent.

8. A therapeutic composition according to claim 7 where the anti-inflammatory therapeutic amount of 6α,9α-difluoro-11β, 17α-21-trihydroxy-16β-methyl-pregna-1,4-diene-3,20-dione 17,21-diacetate if 0.05 percent and the antibacterial therapeutic amount of clindamycin or a pharmaceutically acceptable salt or ester thereof is 1 percent.

9. A therapeutic composition according to claim 8, which is a cream.

10. A therapeutic composition according to claim 8, which is an ointment.

* * * * *